(12) United States Patent
Stark

(10) Patent No.: US 10,054,572 B2
(45) Date of Patent: Aug. 21, 2018

(54) AIR PURIFYING SYSTEM AND A METHOD OF USING THE SAME

(71) Applicant: Carrier Corporation, Farmington, CT (US)

(72) Inventor: Michael M. Stark, Boulder, CO (US)

(73) Assignee: CARRIER CORPORATION, Farmington, CT (US)

(*) Notice: Subject to any disclaimer, the term of this patent is extended or adjusted under 35 U.S.C. 154(b) by 344 days.

(21) Appl. No.: 14/938,507

(22) Filed: Nov. 11, 2015

(65) Prior Publication Data

US 2016/0178586 A1 Jun. 23, 2016

Related U.S. Application Data

(60) Provisional application No. 62/094,738, filed on Dec. 19, 2014.

(51) Int. Cl.
*G01N 33/00* (2006.01)
*B01D 46/44* (2006.01)

(52) U.S. Cl.
CPC ....... *G01N 33/0004* (2013.01); *B01D 46/442* (2013.01)

(58) Field of Classification Search
CPC ...... B01D 46/442; G05F 1/66; G01N 33/0004
See application file for complete search history.

(56) References Cited

U.S. PATENT DOCUMENTS

| | | | |
|---|---|---|---|
| 6,406,367 B1 | 6/2002 | Chou et al. | |
| 7,201,787 B2 | 4/2007 | Choi et al. | |
| 7,292,338 B2 | 11/2007 | Itagaki | |
| 7,366,588 B2 | 4/2008 | Kim et al. | |
| 7,632,178 B2 | 12/2009 | Meneely, Jr. | |
| 7,679,879 B2 | 3/2010 | Furuhashi et al. | |
| 8,157,892 B2 | 4/2012 | Meirav | |
| 8,211,208 B2 | 7/2012 | Chan et al. | |
| 8,596,078 B2 | 12/2013 | Williams et al. | |

(Continued)

FOREIGN PATENT DOCUMENTS

| | | |
|---|---|---|
| CN | 102636621 A | 8/2012 |
| CN | 202802276 U | 3/2013 |

(Continued)

OTHER PUBLICATIONS

Product page on www.grainger.com for the Dayton Humidifier Control, Plug in, 120 V, dated Oct. 18, 2014, retrieved by the Internet Archive Wayback Machine.*

(Continued)

*Primary Examiner* — Robert Clemente
(74) *Attorney, Agent, or Firm* — Cantor Colburn LLP

(57) ABSTRACT

An air quality sensor assembly including a controller, a switching device in communication with the controller, a power receptacle in communication with the switching device, and at least one air quality sensor in communication with the controller, wherein the at least one air quality sensor is configured to measure an air quality value. A method of operating an air purifying system within an interior space of a structure, the method comprising the steps of: operating the controller to create an air purifying condition, determining whether the air purifying condition is present, operating the switching device in a first state if the air purifying condition is present.

23 Claims, 3 Drawing Sheets

(56) References Cited

U.S. PATENT DOCUMENTS

| | | |
|---|---|---|
| 8,607,616 B2 | 12/2013 | Marra |
| 2008/0092745 A1 | 4/2008 | Tsao et al. |
| 2013/0038470 A1 | 2/2013 | Niemeyer et al. |
| 2013/0174646 A1 | 7/2013 | Martin |
| 2013/0178987 A1 | 7/2013 | Meirav et al. |
| 2013/0295835 A1 | 11/2013 | Fleischer et al. |
| 2013/0309154 A1 | 11/2013 | Call et al. |
| 2014/0260692 A1 | 9/2014 | Sharp |
| 2014/0266669 A1 | 9/2014 | Fadell et al. |
| 2014/0277625 A1 | 9/2014 | Gettings et al. |
| 2015/0088331 A1* | 3/2015 | Fiedler .................. G05F 1/66 700/295 |

FOREIGN PATENT DOCUMENTS

| | | |
|---|---|---|
| CN | 203036776 U | 7/2013 |
| CN | 203258769 U | 10/2013 |
| CN | 203414451 U | 1/2014 |
| CN | 203552012 U | 4/2014 |
| CN | 103925676 A | 7/2014 |
| CN | 203687231 U | 7/2014 |

OTHER PUBLICATIONS

Wayback Machine search results for the Dayton Humidifier Control, Plug In, 120 V product page showing archived date of Oct. 18, 2014.*
Friedrich, 5-Stage Air Purifier, Retail Air Purifier Brochure, 2014.
FELLOWES®, Portable Room Air Cleaners (Air Purifiers) : Fellowes AeraMax 100 Air Purifier, Cert. No. AAFC:1209/13/08/01/2080, Feb. 22, 2013.

* cited by examiner

AIR PURIFYING SYSTEM AND A METHOD OF USING THE SAME

CROSS REFERENCE TO RELATED APPLICATIONS

The present application is related to, and claims the priority benefit of, U.S. Provisional Patent Application Ser. No. 62/094,738 filed Dec. 19, 2014, the contents of which are hereby incorporated in their entirety into the present disclosure.

TECHNICAL FIELD OF THE DISCLOSED EMBODIMENTS

The presently disclosed embodiments generally relate to air purification systems, and more particularly, to an air purifying system and a method of using the same.

BACKGROUND OF THE DISCLOSED EMBODIMENTS

Generally, air purifiers and air purification systems designed to remove particulate matter from the air do not naturally provide feedback to a user as it relates to effectiveness. Generally, particulate removal equipment lack a natural feedback and users desire to have acknowledgment that the air purification system is properly operating. There is therefore a need for an air purification system that provides a natural feedback of proper operation.

SUMMARY OF THE DISCLOSED EMBODIMENTS

In one aspect, an air quality sensor assembly is provided. The air quality sensor assembly includes a controller, a switching device in communication with the controller, a power receptacle in communication with the switching device, and at least one air quality sensor in communication with the controller, wherein the at least one air quality sensor is configured to measure an air quality value In one embodiment, the air quality sensor assembly is configured to operate the switching device when an air purifying condition is present. In one embodiment, the air quality sensor assembly includes a display in communication with the controller.

In one aspect, an air purifying system is provided. The air purifying system includes an air purifying device operably coupled to the air quality sensor assembly. In one embodiment, the air purifying device includes a power plug, wherein the power plug is configured to engage the power receptacle of the air quality sensor assembly.

In one aspect, a method of operating the air purifying system is provided. The method includes the step of operating the controller to create an air purifying condition. In one embodiment, the air purifying condition is based at least in part one a desired air quality value. In one embodiment the desired air quality value is adjustable. In another embodiment, the air purifying condition is based at least in part on at least one user defined time. In one embodiment, the at least one user defined time is adjustable.

The method further includes the step of determining whether an air purifying condition is present. In one embodiment, determining whether the air purifying condition is present includes operating the at least one air quality sensor to measure an interior space air quality value; then, the air purifying condition is present when the interior space air quality value is greater than or equal to the desired air quality value. If the air purifying condition is present, the method proceeds to step of operating the switching device in a first state. In one embodiment, operating the switching device in a first state includes allowing power to flow to the power receptacle.

If the air purifying condition is not present, the method proceeds to the step of operating the switching device in a second state. In one embodiment, operating the operating the switching device in a second state includes removing power from the power receptacle.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

DETAILED DESCRIPTION OF THE DISCLOSED EMBODIMENTS

Figure 1:
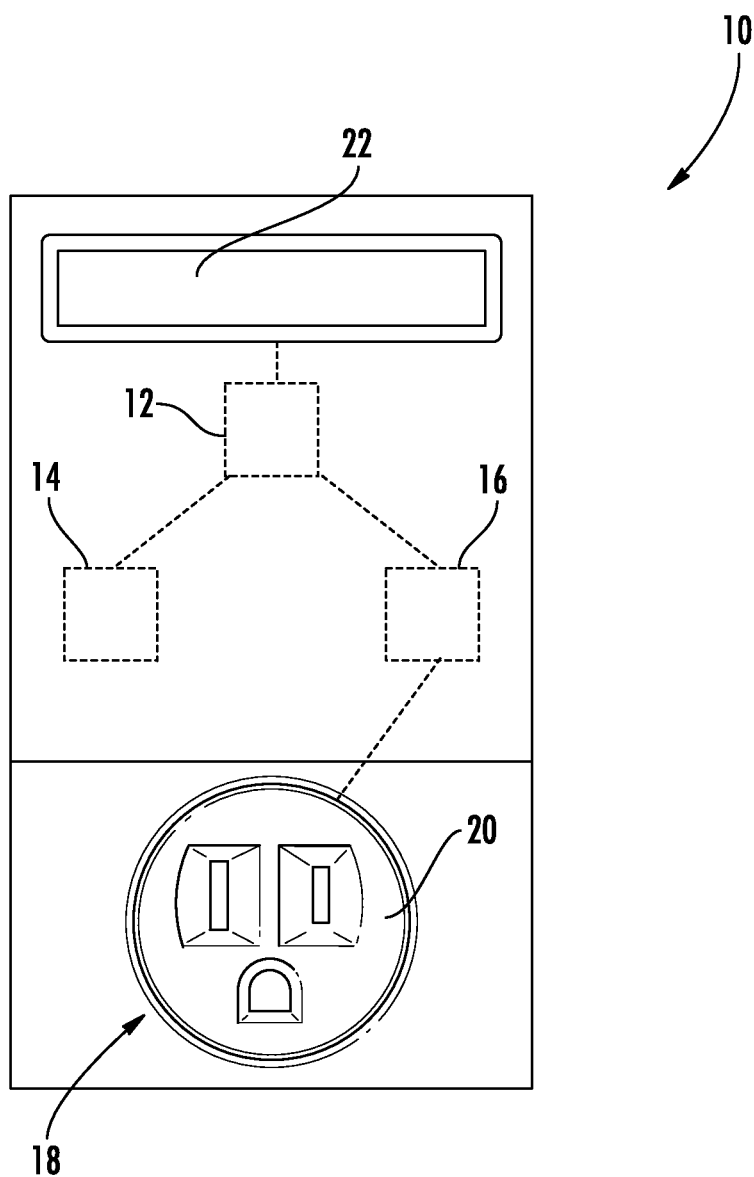
FIG. 1 illustrates a schematic diagram of an air quality sensor assembly according to an embodiment of the present disclosure; assembly.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 illustrates an embodiment of an air quality sensor assembly, generally indicated at 10. The air quality sensor assembly 10 includes a controller 12, at least one air quality sensor 14 in communication with the controller 12, and a switching device 16 in communication with the controller 12. The air quality sensor assembly 10 further includes a power receptacle 18 including a first mating end 20 and a second mating end (not shown), wherein the power receptacle 18 is in communication with the switching device 16. The power receptacle 18 is configured to engage a power plug through the first mating end 20, and engage a wall outlet plug through the second mating end (not shown) to provide power to an air purifying device 36 (See FIG. 2).

The controller 12 is configured to send and receive electrical signals to other components within the air quality sensor assembly 10. The controller 12 is also configured to allow a user to set a desired air quality value. In one embodiment, the desired air quality value is adjustable.

The at least one air quality sensor 14 is configured to detect and measure an air quality value based at least in part on the number of particles detected within the general vicinity of the at least one air quality sensor 14. For example, the at least one air quality sensor 14 may detect and measure dust and volatile organic compounds to name a couple of non-limiting examples. It will be appreciated that the at least one air quality sensor 14 may include an optical sensor for detecting particles. It will also be appreciated that the at least one air quality sensor 14 may detect any such particles that deteriorate the air quality within the interior space 32 (See FIG. 2). The at least one air quality sensor 12 communicates the measured air quality value to the controller 12 in order to determine whether to operate the switching device 16. The switching device 16 is configured to alternate between an open and closed state to provide electrical power to the power receptacle 18. For example, when the measured air quality value is greater than or equal to the desired air quality value, the at least one air quality sensor 14 sends a signal to the controller 12, the controller 12 then sends a signal to the switching device 16 to change from an open state to a closed state. When the measured air quality value becomes lower than to the desired air quality value, the at least one air particle sensor 14 sends a signal to the controller 12, the controller 12 then sends a signal to the switching device 16 to change from a closed to an open state. It will be appreciated that the at least one air quality sensor 14 may send a signal directly to the switching device 16.

In one embodiment, the air quality sensor assembly 10 includes a display 22 in communication with the controller 12. The display 22 is configured to provide an indication to an occupant of the structure 34 (See FIG. 2) of the current level of particles within the interior space 32. For example, the display 22 may include a liquid crystal display (LCD) to provide a numerical value indicative of number of particles within the interior space 32, or the display 22 may include a colored light emitting diode (LED) to indicate whether the measured particles within the interior space are above or below the desired air quality value, to name a couple of non-limiting examples. The display 22 may also be used to provide a visual feedback to the user when setting the desired air quality value.

Figure 2:
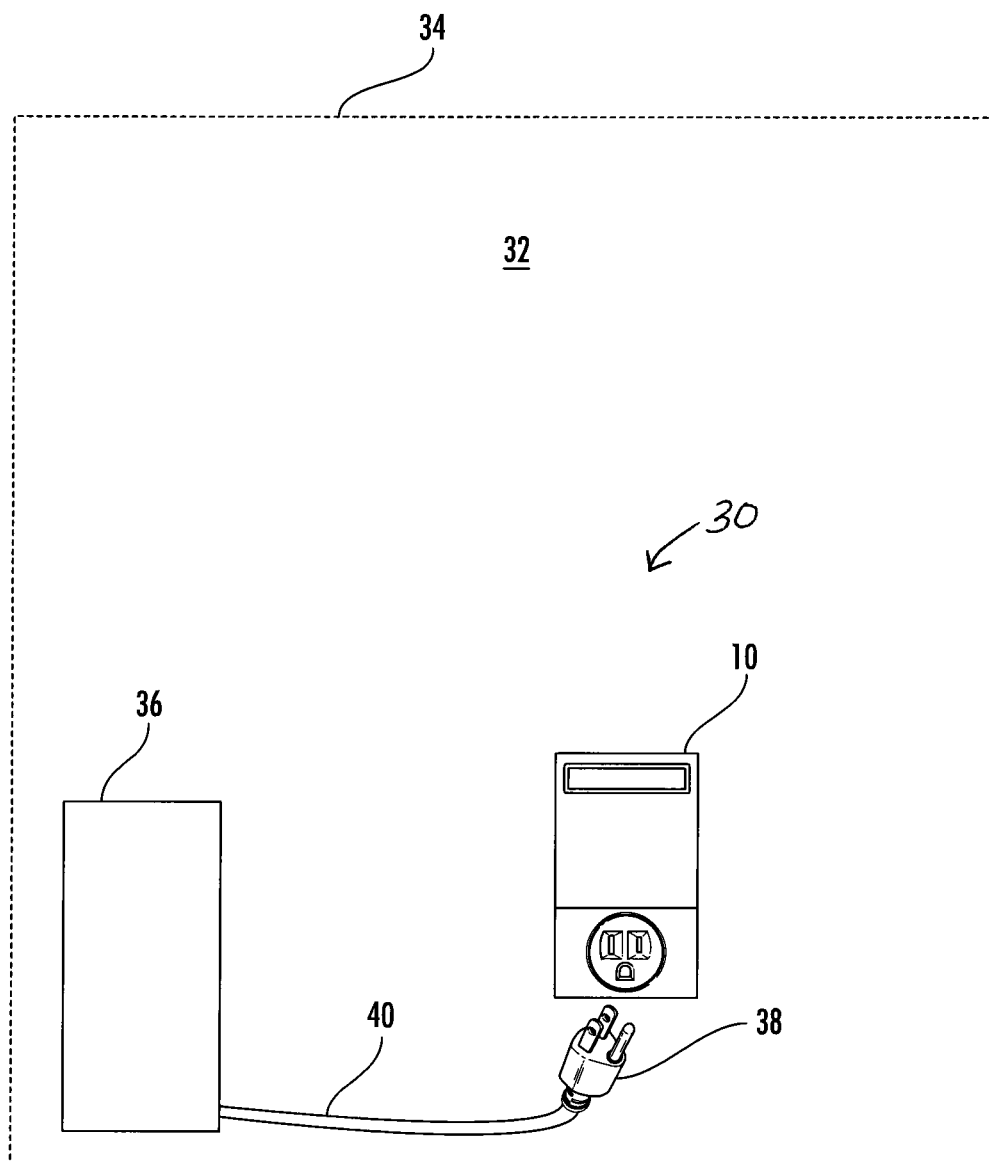
FIG. 2 illustrates a schematic diagram of an air purifying system according to an embodiment of the present disclosure.

FIG. 2 illustrates an embodiment of an air purifying system generally indicated at 30. The air purifying system 30 is configured to improve the indoor air quality of an interior space 32 within a structure 34 The air purifying system 30 includes an air purifying device 36 operably coupled to the air quality sensor assembly 10. The air purifying device 36 is configured to allow air within the interior space 32 to circulate therethrough. The air purifying system 10 further includes an power receptacle 18 in communication with the air purifying device 16. In one embodiment, the air purifying device 36 includes a power plug 38 in electrical communication with the air purifying device 36 via a power cord 40, wherein the power plug 38 is configured to engage the power receptacle 18 of the air quality sensor assembly 10. For example, the power plug 38 may be plugged into the first mating end 20 of the power receptacle 18; the second mating end (not shown) is plugged into a wall outlet to provide power. It will be appreciated that the air purifying device 36 may be a portable air purifier. This configuration allows for a more flexible solution to remove particles within a particular interior space 32.

Figure 3:
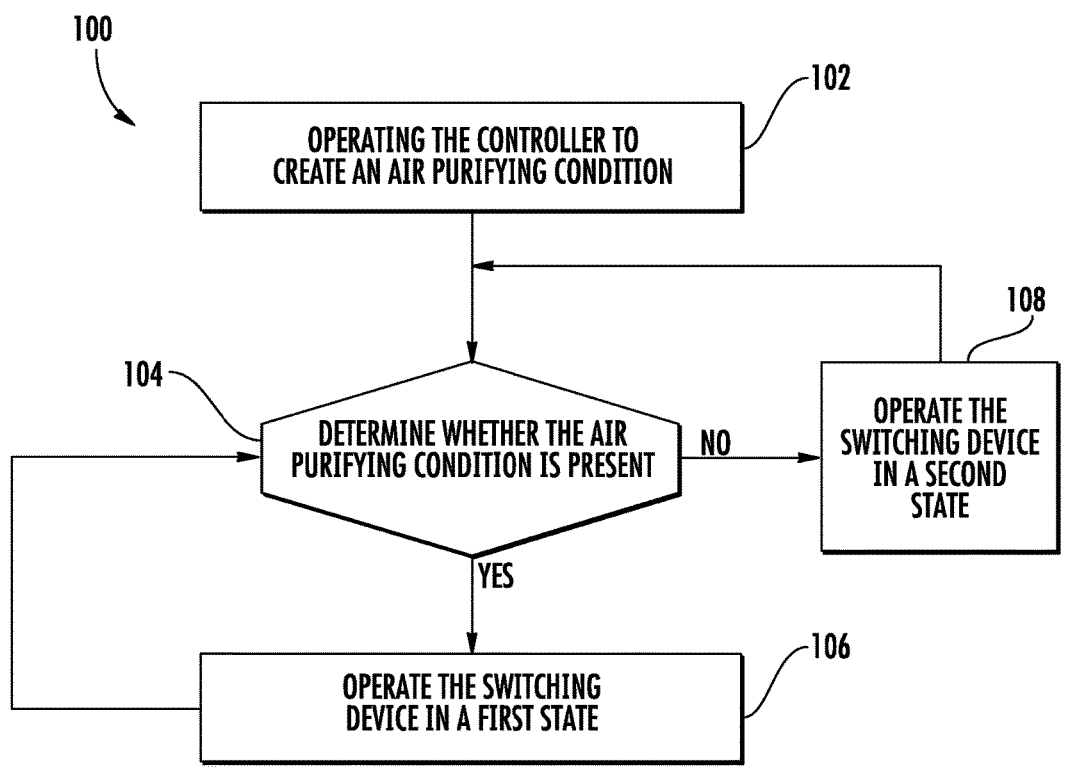
FIG. 3 illustrates a schematic block diagram of a method of operating an air purifying system within an interior space of a structure to an embodiment of the present disclosure.

FIG. 3 illustrates a schematic flow diagram of a method 100 of operating the air purifying system 30 within an interior space 32 of a structure 34. The method 100 includes the step 102 of operating the controller 20 to create an air purifying condition. In one embodiment, the air purifying condition is based at least in part one a desired air quality value. In one embodiment the desired air quality value is adjustable. For example, a user sets a desired air quality value, via the controller 12 within the air quality sensor assembly 10, indicative of the user's preference of the amount of particles present in the interior space 32. The desired air quality value may be shown to the user via the display 22. In another embodiment, the air purifying condition is based at least in part on at least one user defined time. In one embodiment, the at least one user defined time is adjustable. It will be appreciated that the at least one user defined time may include a time of day and/or duration of time, and/or predetermined intervals. For example, the user may set the desired air quality value in accordance to a particular time of day. The user may desire to a lower desired air quality value during periods of time when interior space 32 is occupied, and conversely have a higher desired air quality value when the interior space 32 is unoccupied. In another example, the user may desire to have a higher desired air quality value during sleeping hours such that air purifying device 36 doesn't operate to disrupt the sleep of the user, or the user may desire for the air purifying device 36 to operate at 6:00 pm for a duration of 2 hours, or the user may desire for the air purifying device 36 to operate every 3 hours for 30 minutes.

The method 100 further includes the step 104 of determining whether an air purifying condition is present. In one embodiment, determining whether the air purifying condition is present includes operating the at least one air quality sensor to measure an interior space air quality value; then, the air purifying condition is present when the interior space air quality value is greater than or equal to the desired air quality value. For example value is greater than or equal to the desired air quality value. In another embodiment, the controller 12 compares the measured interior space air quality value to the desired air quality value. If the interior space air quality value is greater than or equal to the desired air quality value, it is an indication that the number of particles within the interior space are outside the user's tolerable threshold.

As a result, the method proceeds to step 106 of operating the switching device 16 in a first state. In one embodiment, operating the switching device 16 in a first state includes allowing power to flow to the power receptacle 18. For example, when the interior space air quality value is greater than or equal to the desired air quality value, the switching device 16 changes from an open state to a closed state to provide power to the power receptacle 18. When the air purifying device 36 is plugged into the air quality sensor assembly 10, air will circulate through the air purifying device 36; thus, removing particles from the interior space 36. The method returns to step 104, until the interior space air quality value is less than the desired air quality value.

If the interior space air quality value is less than the desired air quality value, it is an indication that the number of particles within the interior space are within the user's tolerable threshold, or if the air purifying condition is not present, the method proceeds to step 108 of operating the switching device 16 in a second state. In one embodiment, operating the operating the switching device 16 in a second state includes removing power from the power receptacle 18. For example, when the interior space air quality value is less than the desired air quality value, the switching device 26 changes from a closed state to an open state to remove power from the power receptacle 18. The method returns to step 104 to continue determining whether the air purifying condition is present.

It will therefore be appreciated that the present embodiments include an air quality sensor assembly 10 including a switching device 16 in communication with a power receptacle 18 to allow an air purifying device 36 to be plugged in within any interior space 32 to provide a purification system, on an as needed basis, based on particulate or VOC particles detected in an interior space 32.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. An air quality sensor assembly comprising:
   a controller;
   a switching device in communication with the controller;
   a power receptacle in communication with the switching device; and
   at least one air quality sensor in communication with the controller, wherein the at least one air quality sensor is configured to measure an air quality value based on a number of particles detected by the at least one air quality sensor.

2. The air quality sensor assembly of claim 1, wherein the air quality sensor assembly is configured to operate the switching device when the air quality value is greater than or equal to a desired air quality value.

3. The air quality sensor assembly of claim 1, wherein the air quality sensor assembly is configured to operate the switching device based upon at least one user defined time.

4. The air quality sensor assembly of claim 1, further comprising a display in communication with the controller.

5. The air quality sensor assembly of claim 2, wherein the desired air quality value is adjustable.

6. The air quality sensor assembly of claim 3, wherein the at least one user defined time is adjustable.

7. An air purifying system comprising:
   an air purifying device; and
   an air quality sensor assembly operably coupled to the air purifying device, the air quality sensor assembly comprising:
   a controller;
   a switching device in communication with the controller;
   a power receptacle in communication with the switching device;
   at least one air quality sensor in communication with the controller, wherein the at least one air quality sensor is configured to measure an air quality value based on a number of particles detected by the at least one air quality sensor.

8. The air purifying system of claim 7, wherein the air quality sensor assembly is configured to operate the switching device when the air quality value is greater than or equal to a desired air quality value.

9. The air purifying system of claim 8, wherein the air quality sensor assembly is configured to operate the switching device based upon at least one user defined time.

10. The air purifying system of claim 8, wherein the air quality sensor assembly further comprises a display in communication with the controller.

11. The air purifying system of claim 7, wherein the air purifying device comprises a power plug, wherein the power plug is configured to engage the power receptacle.

12. The air purifying system of claim 8, wherein the desired air quality value is adjustable.

13. The air purifying system of claim 9, wherein the at least one user defined time is adjustable.

14. A method of operating an air purifying system within an interior space of a structure, wherein the air purifying system includes an air purifying device operably coupled to an air quality sensor assembly, the air quality sensor assembly including a controller, a switching device in communication with the controller, a power receptacle in communication with the switching device, and at least one air quality sensor in communication with the controller, wherein the at least one air quality sensor is configured to measure an air quality value, the method comprising the steps of:
   (a) operating the controller to create an air purifying condition;
   (b) determining whether the air purifying condition is present based on a number of particles detected by the at least one air quality sensor; and
   (c) operating the switching device in a first state if the air purifying condition is present.

15. The method of claim 14, further comprising:
   (d) operating the switching device in a second state if the air purifying condition is not present.

16. The method of claim 14, wherein the air purifying condition is based at least in part on a desired air quality value.

17. The method of claim 16, wherein the desired air quality value is adjustable.

18. The method of claim 17, wherein the step (b) further comprises operating the at least one air quality sensor to measure an interior space air quality value.

19. The method of claim 18 wherein the air purifying condition is present when the interior space air quality value is greater than or equal to the desired air quality value.

20. The method of claim 14, wherein the air purifying condition is based at least in part on at least one user defined time.

21. The method of claim 20, wherein the at least one user defined time is adjustable.

22. The method of claim 14, wherein operating the switching device in a first state comprises allowing power to flow to the power receptacle.

23. The method of claim 15, wherein operating the switching device in a second state comprises removing power from the power receptacle.

* * * * *